United States Patent [19]

Fountaine

[11] 4,446,135
[45] May 1, 1984

[54] CHEWABLE ANTACID TABLETS

[75] Inventor: Harvey A. Fountaine, East Greenbush, N.Y.

[73] Assignee: Sterling Drug Inc., New York, N.Y.

[21] Appl. No.: 385,913

[22] Filed: Jun. 7, 1982

[51] Int. Cl.³ .................... A61K 33/06; A61K 33/08; A61K 33/10

[52] U.S. Cl. .................................. 424/154; 424/156; 424/157

[58] Field of Search .................................. 424/48–58, 424/154–158

[56] References Cited

U.S. PATENT DOCUMENTS

| | | | |
|---|---|---|---|
| Re. 29,634 | 5/1978 | Roberts et al. | 424/49 |
| 3,384,546 | 5/1968 | Palermo . | |
| 3,843,778 | 10/1974 | Diamond et al. . | |
| 4,115,553 | 9/1978 | Rubino et al. . | |
| 4,327,076 | 4/1982 | Puglia et al. | 424/38 |
| 4,327,077 | 4/1982 | Puglia et al. | 424/38 |

FOREIGN PATENT DOCUMENTS

| | | | |
|---|---|---|---|
| 2922671 | 4/1980 | Fed. Rep. of Germany | 424/57 |
| 53-32133 | 3/1978 | Japan | 424/49 |
| 54-140740 | 1/1979 | Japan | 424/49 |
| 1056212 | 1/1967 | United Kingdom . | |
| 1401256 | 7/1975 | United Kingdom . | |
| 1572164 | 7/1980 | United Kingdom | 424/52 |

OTHER PUBLICATIONS

Rider et al., Clinical Med., 73, 44–46 (1966).
Broda et al., Farm. Pol., 36 (4), 215–219 (1980); C.A., 93, 173683 (1980).
Van de Loo, Munchen med. Wschr., 118, 271–274 (1976).
Smyth et al., J. Pharm. Sci., 65 (7), 1045–1047 (1976).
Madee et al., Arzneimittel Forsch., 25 (1), 122–123 (1975).
Salakawy et al., Pharmazie 27 (9), 595–599 (1972).

*Primary Examiner*—Shep K. Rose
*Attorney, Agent, or Firm*—William G. Webb; B. Woodrow Wyatt

[57] ABSTRACT

Chewable calcium carbonate-containing antacid tablets having good "mouthfeel" contain calcium carbonate particles of a particular size in combination with certain excipients.

5 Claims, No Drawings

CHEWABLE ANTACID TABLETS

BACKGROUND OF THE INVENTION (a) Field of the Invention

This invention relates to chewable calcium carbonate-containing antacid tablets.

(b) Description of the Prior Art

The use of calcium carbonate as the effective acid neutralizing agent in antacid tablets is known. The problem with calcium carbonate as an ingredient in antacid tablets, however, is that, unless formulated in special ways, it produces tablets which taste gritty and chalky and which thus lack the desirable quality in chewable antacid tablets known as good "mouthfeel". The problem of overcoming this undesirable gritty and chalky taste in chewable calcium carbonate-containing antacid tablets has either been ignored by the prior art, or the problem has been addressed by use of flavoring agents or other ingredients intended to mask the undesirable taste.

Thus neither Palermo, U.S. Pat. No. 3,384,546, which discloses, in Example 6, a chewable antacid tablet containing calcium carbonate, magnesium trisilicate, mannitol, sorbitol, sodium saccharin, mint flavoring and magnesium stearate, nor British Pat. No. 1,056,212 which discloses the use of a combination of urea and glycine as an extended buffering agent for calcium carbonate, addresses the question of the chalky taste of calcium carbonate containing antacids.

Diamond et al., U.S. Pat. No. 3,843,778, which discloses the use of calcium carbonate as one of several "preferred" ingredients for antacids, overcomes the taste problem by coating the calcium carbonate particles with oil. The particle size of the antacid ingredient is disclosed as being in the range from 0.5 to 300 microns, although no reason for the particular choice of particle size is given. In British Pat. No. 1,401,256 the chalky taste of calcium carbonate-containing antacids is overcome by spray drying the calcium carbonate with a surfactant which also aids in dissolution of the tablet.

Granatek, U.S. Pat. No. 3,452,138 teaches that mannitol provides a very astringent tablet which must be taken with water, while Rubino, U.S. Pat. No. 4,115,553 discloses the use of basic aluminum bicarbonate/carbonate co-dried with a di- or trihydroxyalcohol to provide chewable antacid tablets with a good disintegration rate. The use of mannitol alone or in combination with sorbitol is also described, and sucrose is disclosed as an excipient that can be used either instead of, or in combination with, mannitol.

A number of publications have reported studies comparing the relative antacid efficacies of calcium carbonate and other acid neutralizing agents. For example Rider et al., Clin. Med., 73, 44–46 (1966) describe comparative tests in patients suffering from various stomach ailments using antacid tablets made either from calcium cabonate, magnesium carbonate or a powdered milk/cream formula; Broda et al., Farm. Pol., 36(4), 215–219 (1980); C.A., 93, 173683g (1980) describe tests to determine the relative acid neutralizing capabilities of different antacids containing either magnesium oxide, aluminum hydroxide, magnesium carbonate, basic bismuth nitrate, magnesium hydroxide, calcium carbonate or sodium bicarbonate; Van de Loo, Munchen med. Wschr., 118, 271–274 (1976) report the results of the clinical treatment of ulcerous diseases with antacids containing either aluminum hydroxide, magnesium carbonate or calcium carbonate; and Smyth et al., J. Pharm. Sci., 65 (7), 1045–1047 (1976) disclose the results of a study of the correlation between in vitro and in vivo methods for assessing antacids containing either magnesium hydroxide, aluminum hydroxide or calcium carbonate.

Other publications have reported studies on various physical properties of calcium carbonate-containing antacids. For example Madee et al., Arzneimittel Forsch., 25 (1), 122–123 (1975) report a comparison of the disintegration rates, as measured by an intragastric pH probe, of two formulations of calcium carbonate-containing antacid tablets, one in which the particles were wax coated and the other in which they were uncoated; and Salakawy et al., Pharmazie, 27 (9), 595–599 (1972) report the results of a study of the cause of darkening of calcium carbonate/glycine-containing antacid tablets in the presence of aldo or keto sugars.

BRIEF SUMMARY OF THE INVENTION

It has now been found that the gritty and chalky taste of chewable calcium carbonate containing antacid tablets is due in very large part to the size of the calcium carbonate particles. That is, large sized particles have an inherent grittiness due entirely to the size of the particles, while smaller sized particles, quite surprisingly, tend to agglomerate during wet granulation into larger sized particles which likewise have the gritty and chalky taste.

Accordingly, the present invention is directed to chewable calcium carbonate-containing antacid tablets in which the undesirable chalky/gritty taste is overcome by use of calcium carbonate of a particular particle size in combination with certain excipients.

DETAILED DESCRIPTION OF THE INVENTION

More particularly, the invention relates to a chewable calcium carbonate-containing antacid tablet formulation containing, in a primary granulation, calcium carbonate and magnesium hydroxide, as the effective antacid ingredients, and wherein the calcium carbonate particles are of a certain critical size, namely from 5 to 50 microns, and preferably around 15 microns in diameter, and further containing sucrose and mannitol. The primary granulation is then formulated into a final tablet mixture containing minor amounts of a flavoring agent and a tablet lubricating agent, such as magnesium stearate.

The chalky and gritty taste usually associated with calcium carbonate-containing chewable antacid tablets is totally lacking in tablets prepared according to the present invention which have unusually good "mouthfeel". Other advantages which are inherent in the formulation and the preparation of antacid tablets therefrom are: (1) the preparation of the tablet mixture can be carried out in conventional milling and blending equipment and (2) the formulation procedure is more economical, because less water is needed in the granulation process using the particular size of calcium carbonate required by the invention. Thus a shortened drying time is required in granulation.

In the practice of this invention a primary tablet granulation composed of:

|  | % w/w |
| --- | --- |
| Calcium Carbonate | 45-50 |
| Magnesium Hydroxide | 8-11 |
| Sucrose | 30-40 |
| Mannitol | 8-11 | is first blended thoroughly and then wet granulated with about 50 ml. of water per kilogram of the thus prepared solid primary granulation. After blending and drying, the primary granulation is then blended with minor amounts of a flavoring agent and a tablet lubricating agent and then pressed into tablets in conventional tabletting equipment. The final tablet mixture contains, in weight percent of the final tablet mixture, from 95 to 98% of the primary granulation described above; from 1.2 to 2.0% of a tablet lubricating agent; and from 0.2 to 0.5% of a flavoring agent.

In a preferred formulation, the primary granulation contains from 45 to 47% fo calcium carbonate; from 9 to 10% of magnesium hydroxide; from 33 to 36% of sucrose and from 9 to 10% of mannitol, while the final tablet formulation contains up to 98% of primary granulation; around 1.4 to 1.8% of a lubricating agent; and the remainder flavoring agent.

The preparation of a specific tablet formulation according to the present invention will now be described so as to enable any person skilled in the art to practice the invention.

A mixture of 11.7 kg. of calcium carbonate having an average particle size of 15 microns; 2.40 kg. of magnesium hydroxide; 3.64 kg. of sucrose; and 2.30 kg. of mannitol was passed through a Fitzmill with a number "0" drill plate at high speed with the hammers forward. The mixture was then blended in a blender for fifteen minutes, wet granulated with 1250 ml. of purified water and the wet granulation reduced through a D4A plate at high speed with the knives forward. The granulation was then dried at 50° C. and, after drying, was reduced through a 2B plate at medium speed with the knives forward.

The thus prepared primary granulation was then formulated into a final tablet mix as follows: A mixture of 6.26 kg. of the primary granulation; 0.025 kg. of guarana mint flavor and 0.090 kg. of magnesium stearate was prepared, the mint flavor and magnesium stearate having first been passed through a 40 mesh silk screen. The mixture thus prepared was blended for fifteen minutes and then compressed into tablets in a conventional tabletting machine. The tablets thus prepared were smooth with no machine-caused irregularities, and showed a hardness of about 4.0 kg. and fair fragility (1 tablet broken, some chipping on others).

The tablets thus prepared had an unusually good "mouthfeel" with a complete lack of a gritty and chalky taste.

Having thus described the invention, what it is desired to claim as the invention is as follows:

1. In a method of imparting good "mouthfeel" in chewable antacid tablets, said good "mouthfeel" being characterized by a non-chalky, non-gritty texture, said tablets being prepared from a primary granulation of tablet ingredients comprising from 45 to 50 weight percent of calcium carbonate and from 8 to 11 weight percent of magnesium hydroxide, as the effective antacid ingredients, along with from 30 to 40 weight percent of sucrose and from 8 to 11 weight percent of mannitol, said primary granulation, together with a flavoring agent and a tablet lubricating agent, being pressed into said chewable tablets, the improvement which comprises use of calcium carbonate having an average particle diameter from 5 to 50 microns to impart said good "mouthfeel" to said chewable tablets.

2. A method according to claim 1 wherein said primary granulation contains from 45 to 47 weight percent of calcium carbonate, from 9 to 10 weight percent of magnesium hydroxide, from 33 to 36 weight percent of sucrose and from 9 to 10 weight percent of mannitol.

3. A method according to claim 2 wherein the calcium carbonate particles have an average diameter of 15 microns.

4. A method according to claim 3 wherein the final tablet mixture contains from 95 to 98 weight percent of the primary granulation, from 1.2 to 2.0 weight percent of a tablet lubricating agent and from 0.2 to 0.5 weight percent of a flavoring agent.

5. A method according to claim 4 wherein the tablet lubricating agent is magnesium stearate and the flavoring agent is mint.

* * * * *